(12) United States Patent
Trzecieski

(10) Patent No.: US 10,537,690 B2
(45) Date of Patent: Jan. 21, 2020

(54) DEVICE FOR VAPORIZATION OF CONCENTRATED PHYTO MATERIAL EXTRACTS

(71) Applicant: Michael Alexander Trzecieski, Toronto (CA)

(72) Inventor: Michael Alexander Trzecieski, Toronto (CA)

(73) Assignee: Vapium Inc., Toronto (CA)

( * ) Notice: Subject to any disclaimer, the term of this patent is extended or adjusted under 35 U.S.C. 154(b) by 528 days.

(21) Appl. No.: 15/240,203

(22) Filed: Aug. 18, 2016

(65) Prior Publication Data

US 2017/0065776 A1   Mar. 9, 2017

Related U.S. Application Data

(60) Provisional application No. 62/215,168, filed on Sep. 8, 2015.

(51) Int. Cl.
*A61M 11/04* (2006.01)
*H05B 3/46* (2006.01)
(Continued)

(52) U.S. Cl.
CPC ............ *A61M 11/042* (2014.02); *A24F 1/30* (2013.01); *A24F 1/32* (2013.01); *A61M 15/0021* (2014.02);
(Continued)

(58) Field of Classification Search
CPC ...... A24F 1/02; A24F 1/14; A24F 1/30; A24F 1/32; A24F 47/00; A24F 47/008; A61B 34/30; A61L 9/00; A61L 9/03; A61M 11/041; A61M 11/042; A61M 11/044; A61M 11/048; A61M 15/0021; A61M 15/0036; A61M 15/0065; A61M 15/06; A61M 15/08; A61M 16/16; A61M 2021/0016; A61M 21/02; A61M 2205/0211; A61M 2205/215; A61M 2205/3334; A61M 2205/3368; A61M 2205/3372; A61M 2205/3375; A61M 2205/3553; A61M 2205/3569; A61M 2205/3584; A61M 2205/3592; A61M 2205/3653; A61M 2205/368; A61M 2205/50; A61M 2205/502; A61M 2205/58; A61M 2205/581; A61M 2205/583; A61M 2205/584; A61M 2205/587; A61M 2205/80; A61M 2205/8206; A61M 2209/045; A61M 2209/084; A61M 2209/086; F23Q 7/22; H05B 2203/021; H05B 3/46

See application file for complete search history.

(56) References Cited

U.S. PATENT DOCUMENTS

| 4,133,318 A | 1/1979 | Gross et al. |
|---|---|---|
| 10,004,264 B2 | 6/2018 | Rado |

(Continued)

OTHER PUBLICATIONS

Dixon, Annette Fredricka. "Office Action", dated Aug. 19, 2019. U.S. Appl. No. 15/453,001. 27 pages.
(Continued)

*Primary Examiner* — Annette Dixon
(74) *Attorney, Agent, or Firm* — Bereskin & Parr LLP/S.E.N.C.R.L., s.r.l.

(57) ABSTRACT

A novel device for vaporization of concentrated phyto material extracts is disclosed having a vaporization element for being fluidly coupled with an input port of a waterpipe. The vaporization element having a resistive heater for heating of phyto material extract for vaporization thereof and for inhalation of vapor from an inhalation aperture of the waterpipe. The device for vaporization of concentrated phyto material extracts having an adjustable clamping mechanism and a plurality of batteries for powering of the resistive heater.

22 Claims, 11 Drawing Sheets

(51) Int. Cl.
*A24F 1/30* (2006.01)
*A24F 1/32* (2006.01)
*A61M 15/00* (2006.01)

(52) U.S. Cl.
CPC ....... *H05B 3/46* (2013.01); *A61M 2205/0211* (2013.01); *A61M 2205/3368* (2013.01); *A61M 2205/3653* (2013.01); *A61M 2205/502* (2013.01); *A61M 2205/584* (2013.01); *A61M 2205/8206* (2013.01); *H05B 2203/021* (2013.01)

(56) References Cited

U.S. PATENT DOCUMENTS

| | | |
|---|---|---|
| 10,021,909 B2 | 7/2018 | Rado |
| 10,321,721 B2 | 6/2019 | Rado |
| 10,327,470 B2 | 6/2019 | Rado |
| 2006/0086364 A1 | 4/2006 | Liu |
| 2009/0095310 A1 | 4/2009 | Chaoui |
| 2011/0308521 A1* | 12/2011 | Kofford ............... A61M 11/041 128/203.27 |
| 2013/0032159 A1* | 2/2013 | Capuano ................. A24F 1/30 131/329 |
| 2014/0083441 A1* | 3/2014 | Kaplani ................ A24F 47/008 131/329 |
| 2014/0130812 A1* | 5/2014 | Kling .................... A24F 47/008 131/173 |
| 2014/0255014 A1 | 9/2014 | Bishara |
| 2016/0066619 A1 | 3/2016 | Di Carlo |
| 2016/0030692 A1 | 4/2016 | Burk et al. |
| 2016/0206001 A1 | 7/2016 | Eng et al. |
| 2017/0055579 A1 | 3/2017 | Kuna et al. |
| 2018/0110938 A1 | 4/2018 | Trzecieski |
| 2018/0221604 A1 | 8/2018 | Trzecieski |

OTHER PUBLICATIONS

Dixon, Annette Fredricka. "Office Action", dated Aug. 20, 2019. U.S. Appl. No. 15/626,656, 14 pages.

\* cited by examiner

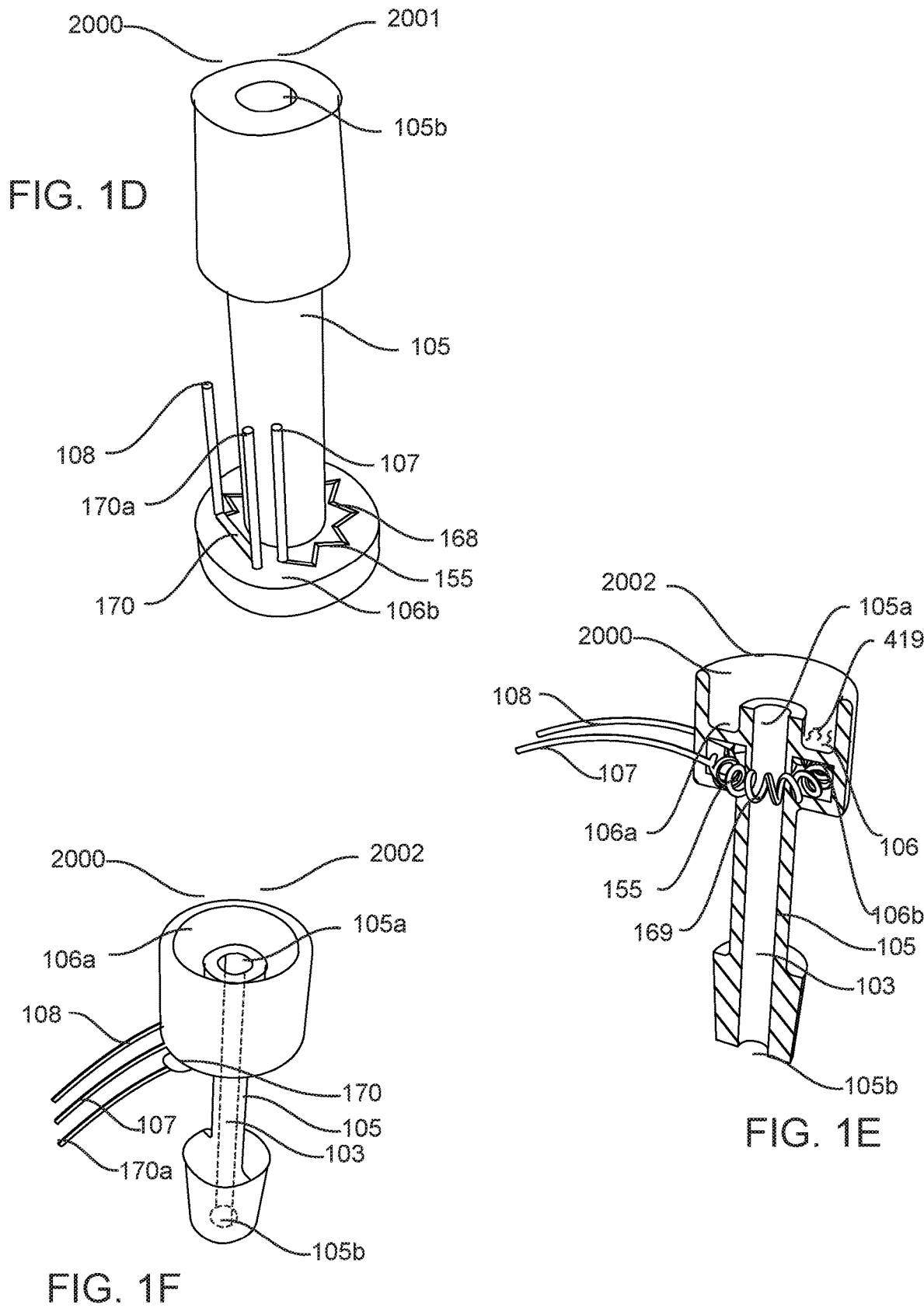

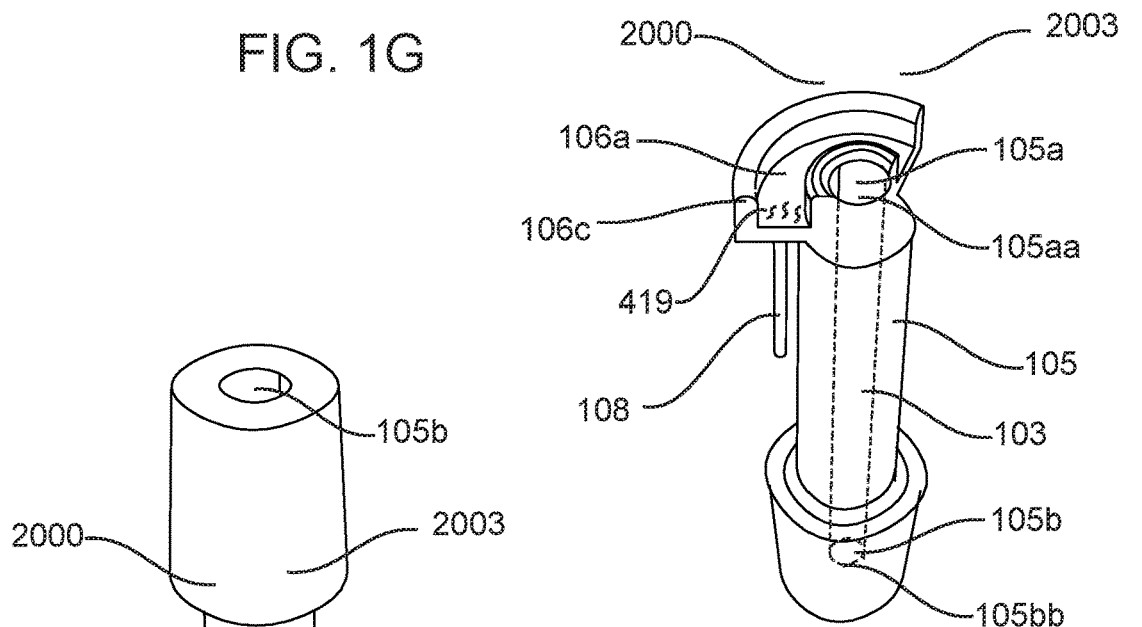
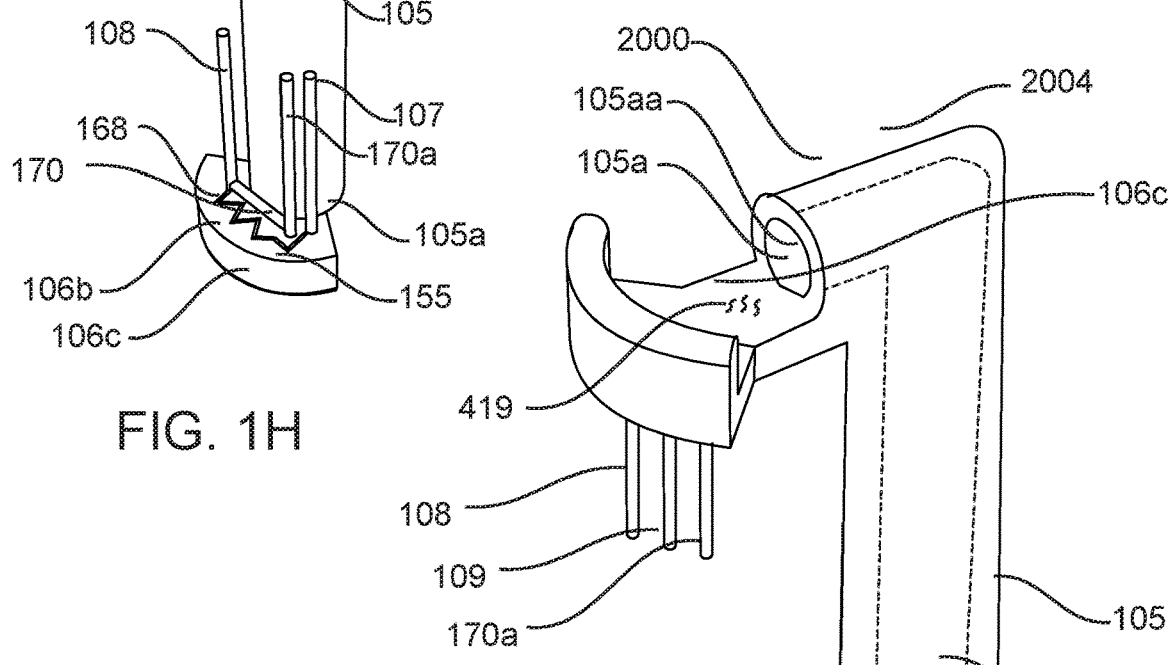
FIG. 1G
FIG. 1H
FIG. 1I

DEVICE FOR VAPORIZATION OF CONCENTRATED PHYTO MATERIAL EXTRACTS

CROSS REFERENCE TO RELATED APPLICATION

This application benefits from the priority of U.S. Provisional Applications 62/215,168 filed on Sep. 8, 2015, which is incorporated herein by reference.

TECHNICAL FIELD OF THE INVENTION

The technical field relates to a device for vaporization of phyto materials and more specifically to a device for vaporization of phyto material extracts.

BACKGROUND OF THE INVENTION

Aromatherapy generally uses essential oils, which are extracted from phyto materials, such as leaves of plants, for therapeutic benefits. These essential oils are either massaged into the skin or can be inhaled. In some cases the phyto materials are heated in order to released the essential oils therefrom. By heating these phyto materials at predetermined temperatures, essential oils and extracts are boiled off, depending upon the temperature at which these phyto materials are heated, an aroma or vapor is given off, which is then inhaled by a user for its therapeutic benefits. Devices that provide such operation are generally known as vaporizers. There are also extracts available that are derived from the phyto material or loose-leaf aromatherapy materials and these have a consistency of honey and are typically highly purified forms. Normally these extracts are vaporized at temperatures between 500 to 700 degrees Fahrenheit.

Devices that process these concentrated phyto material extracts typically include a waterpipe, or bong, that has an input port and an inhalation aperture with a fluid pathway formed therebetween. Normally a metal or ceramic vaporization element is inserted into the input port and it is heated with a torch to get it to reach a temperature of about 500 to 700 degrees Fahrenheit. Measurement of the temperature of the vaporization element is not measured and usually the process is a visual or time based one. Phyto material extract is applied to the vaporization element and a user inhales from the inhalation aperture of the waterpipe, which results in vaporized phyto material and ambient air to flow into the inhalation aperture and into the fluid pathway for being cooled by the water which is typically disposed within this fluid pathway to cool the vapor air mixture.

Because the heating is performed by a torch, such devices do not typically vaporize the concentrated phyto material extracts and instead combust them. Heating to combustion temperatures usually results in smoke and other combustion by products to be inhaled therefrom. This combustion of course isn't a safe process as there are many harmful byproducts released in the combustion process. Glass or ceramic vaporization elements are preferable as these materials offer an experience that affects a taste of the vapor the least.

There are other solutions on the market that utilize a metal nail with a heater coil wrapped around it that are normally plugged into a wall, however these devices are cumbersome and not power efficient because of an amount of thermal mass that needs to be heated in order to attain a required vaporization temperature of the heated member. They are also not appealing in product design and can lead to end users tripper over the power supply cables. Not to mention that these devices are also not portable.

It is therefore an object of the invention to provide an aromatherapy vaporization device that overcomes the aforementioned deficiencies.

SUMMARY

In accordance with the embodiments of the invention there is provided a device for vaporization of concentrated phyto material extracts for attaching to a waterpipe having an input port and an inhalation aperture with a waterpipe fluid pathway formed therebetween comprising: a vaporization element comprising: an elongated hollow member formed from a low thermal conductivity material having a first end and a second end opposite the first end, a fluid pathway propagating through the elongated hollow member from the first end to the second end thereof, the second end for coupling with the waterpipe input port; an annular heating element having a first side and a second side opposite the first side, the annular heating element thermally coupled with the elongated hollow member proximate the first end and having the first side facing the first end with the fluid pathway propagating through a center thereof, the annular heating element comprising a first electrical contact and a second electrical contact proximate the second side, the annular heating element secured to the elongated hollow member for allowing thermal expansion thereof along a radial axis perpendicular to the fluid pathway, the annular heating element comprising a resistive heater disposed between the first and second electrical contacts and proximate the second side; and an electrical power source electrically coupled with the first and second electrical contacts for providing of electrical power to the resistive heater for heating of the resistive heater for imparting thermal energy to the annular heating element, wherein during heating of the resistive heater, a portion of the thermal energy is transferred to the annular heating element first side and another portion, other than the first portion, is transferred to the elongated hollow member proximate the first end, upon the annular heating element second side reaching a predetermined temperature the concentrated phyto material extract is applied to the annular heating element first side and becomes vaporized and upon inhalation from the inhalation aperture this vapor is mixed with ambient air and flows through the fluid pathway from the first end where it loses thermal energy to the elongated hollow member proximate the second end as it propagates through the input port of the waterpipe and through the waterpipe fluid pathway and to the inhalation aperture.

In accordance with the embodiments of the invention there is provided a device for vaporization of concentrated phyto material extracts for attaching to a waterpipe having an input port and an inhalation aperture with a waterpipe fluid pathway formed therebetween comprising: a vaporization element comprising: an elongated hollow member formed from a low thermal conductivity material having a first end and a second end opposite the first end, a fluid pathway propagating through the elongated hollow member from the first end to the second end thereof, the second end for coupling with the waterpipe input port; an annular heating element having a first side and a second side opposite the first side, the annular heating element thermally coupled with the elongated hollow member proximate the first end and having the first side facing the first end with the fluid pathway propagating through a center thereof, the annular heating element comprising a first electrical contact and a second electrical contact proximate the second side, the annular heating element secured to the elongated hollow member using silica and for allowing thermal expansion of the annular heating element along a radial axis perpendicular to the fluid pathway, the annular heating element comprising a metallic planar heater disposed on the second side between the first and second electrical contacts; an electrical power source comprising a plurality of batteries electrically coupled with a first control circuit, which is electrically coupled with the first and second electrical contacts for controllably providing of electrical power to the metallic planar heater for heating of the metallic planar heater for imparting thermal energy to the annular heating element, wherein during heating of the metallic planar heater, a portion of the thermal energy is transferred to the annular heating element first side and another portion, other than the first portion, is transferred to the elongated hollow member proximate the first end, upon the annular heating element second side reaching a predetermined temperature the concentrated phyto material extract is applied to the annular heating element first side and becomes vaporized and upon inhalation from the inhalation aperture this vapor is mixed with ambient air and flows through the fluid pathway from the first end where loses thermal energy to the elongated hollow member proximate the second end as it propagates through the input port of the waterpipe and through to the waterpipe fluid pathway and through the inhalation aperture; and a first housing for having the electrical power source contained there and the plurality of batteries, the first housing comprising an adjustable clamping mechanism for frictionally engaging of the waterpipe.

In accordance with the embodiments of the invention there is provided a device for vaporization of concentrated phyto material extracts for attaching to a waterpipe having an input port and an inhalation aperture with a waterpipe fluid pathway formed therebetween comprising: a vaporization element comprising: an elongated hollow member formed from a low thermal conductivity material having a first end and a second end opposite the first end, a fluid pathway propagating through the elongated hollow member from the first end to the second end thereof, the second end for coupling with the waterpipe input port; a partial annular heating element radially disposed about the elongated hollow member, the partial annular heating element having a first side and a second side opposite the first side, the partial annular heating element thermally coupled with the elongated hollow member proximate the first end and having the first side facing the first end with the fluid pathway propagating through a center thereof, the partial annular heating element comprising a first electrical contact and a second electrical contact proximate the second side, the partial annular heating element secured to the elongated hollow member for allowing thermal expansion thereof along a radial axis perpendicular to the fluid pathway, the partial annular heating element comprising a resistive heater disposed between the first and second electrical contacts and proximate the second side; an electrical power source electrically coupled with the first and second electrical contacts for providing of electrical power to the resistive heater for heating of the resistive heater for imparting thermal energy to the partial annular heating element, wherein during heating of the resistive heater, a portion of the thermal energy is transferred to the partial annular heating element first side and another portion, other than the first portion, is transferred to the elongated hollow member proximate the first end, upon the partial annular heating element second side reaching a predetermined temperature the concentrated phyto material extract is applied to the partial annular heating element first side and becomes vaporized and upon inhalation from the inhalation aperture this vapor is mixed with ambient air and flows through the fluid pathway from the first end where loses thermal energy to the elongated hollow member proximate the second end as it propagates through the input port of the waterpipe and through the waterpipe fluid pathway and through to the inhalation aperture.

BRIEF DESCRIPTION OF THE DRAWINGS

FIG. 1D illustrates a bottom view of an annular heating element as part of the first vaporization element;

FIG. 1E illustrates a perspective view of a vaporization element in the form of a second vaporization element;

FIG. 1F illustrates a cutaway view of a vaporization element in the form of a second vaporization element;

FIG. 1G illustrates a perspective view of a vaporization element in the form of a third vaporization element having a partial annular heating element;

FIG. 1H illustrates a bottom view of a vaporization element in the form of a third vaporization element having a partial annular heating element;

FIG. 1I illustrates a perspective view of a variation of the third vaporization element having a partial annular heating element and a curved fluid pathway;

DETAILED DESCRIPTION OF EMBODIMENTS OF THE INVENTION

Figure 2A:
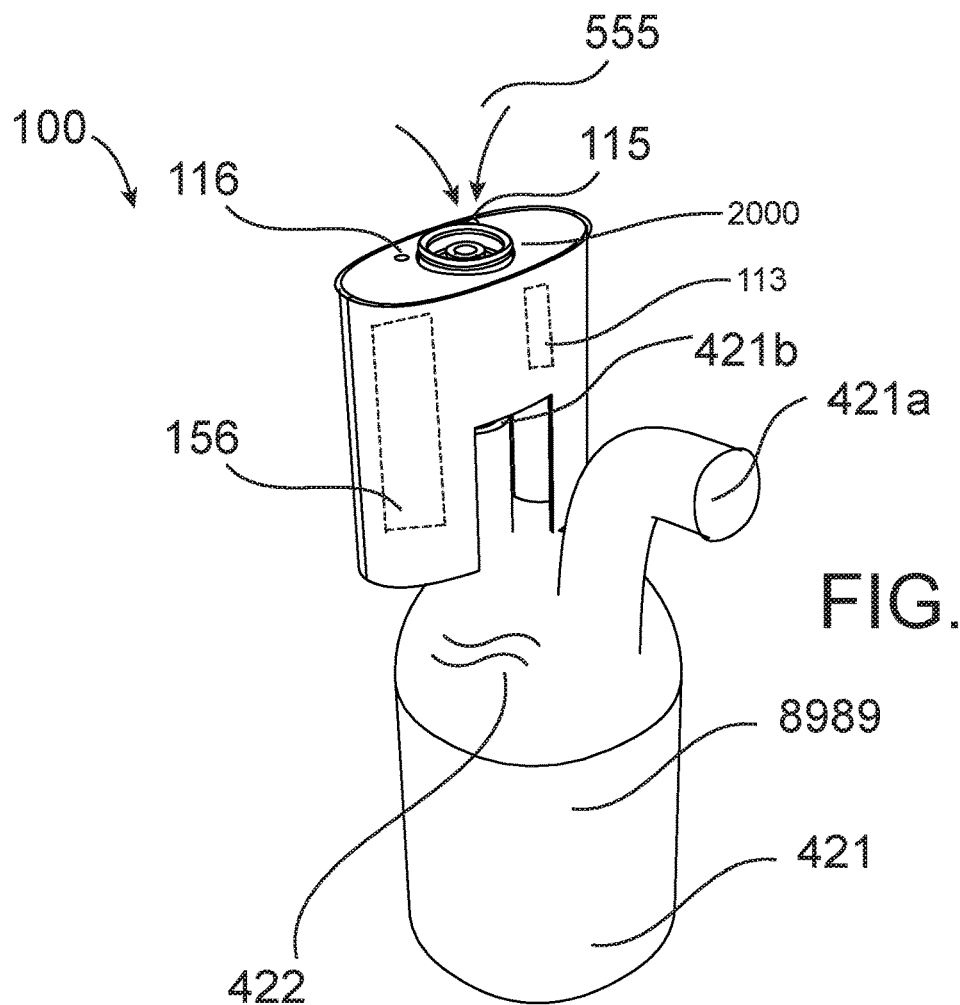
FIG. 2A illustrates a perspective view of device for vaporization of concentrated phyto material extracts coupled with a waterpipe and in accordance with a first embodiment of the invention.
Figure 3A:
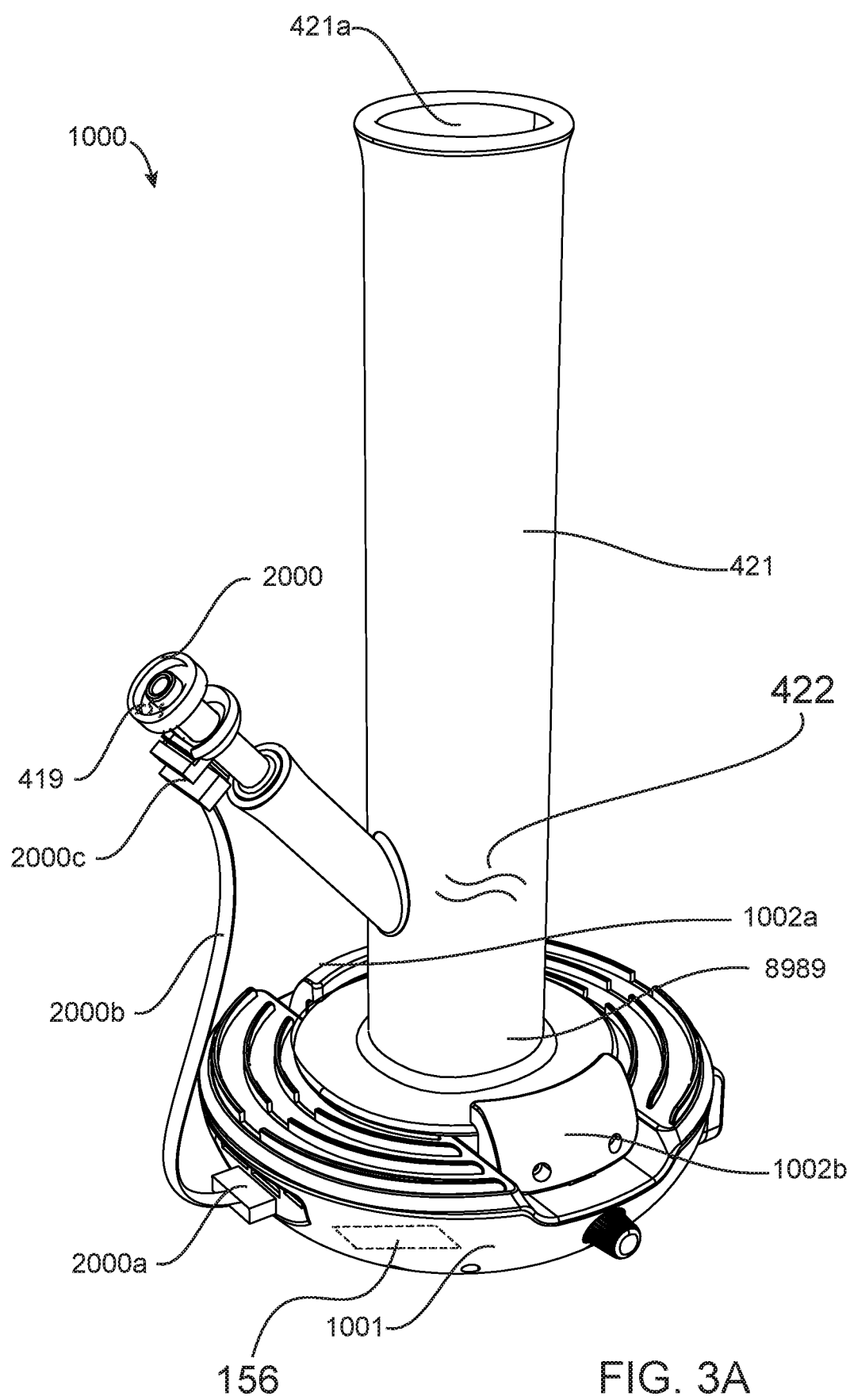
FIG. 3A illustrates a device for vaporization of concentrated phyto material extracts in accordance with a second embodiment of the invention and attached to a waterpipe.

FIG. 2A illustrates a device for vaporization of concentrated phyto material extracts 100 (DVCPM) in accordance with a first embodiment of the invention. The DVCPM 100 is for attaching to a waterpipe 421 having an input port 421b and an inhalation aperture 421a with a waterpipe fluid pathway 8989 formed therebetween. FIG. 3A illustrates a device for vaporization of concentrated phyto material extracts 1000 (DVCPM) in accordance with a second embodiment of the invention. The DVCPM 1000 is for attaching to a waterpipe 421 having an input port 421b and an inhalation aperture 421a with the waterpipe fluid pathway 8989 formed therebetween.

Referring to FIGS. 1A, 1B, 1C, 1D a vaporization element 2000 is shown in the form of a first vaporization element 2001. FIGS. 1E and 1F illustrate a vaporization element 2000 in the form of a second vaporization element 2002 and FIGS. 1G and 1H illustrates a vaporization element 2000 in the form of a third vaporization element 2003. FIG. 1I illustrates a vaporization element 2000 in the form of a fourth vaporization element 2004 that is a variation of the third vaporization element 2003. Throughout the detailed description, the vaporization element 2000 is for use in both of the first and second embodiments of the invention, DVCPM 100 and DVCPM 1000, respectively.

Figure 1A:
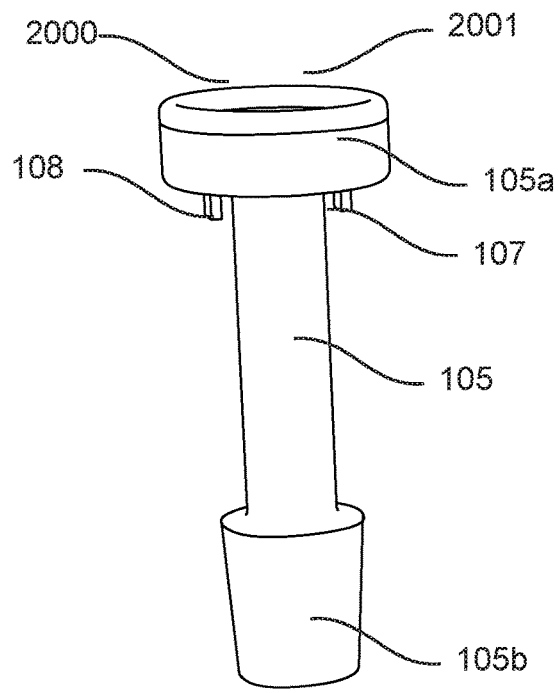
FIG. 1A illustrates a vaporization element in the form of a first vaporization element.
Figure 1B:
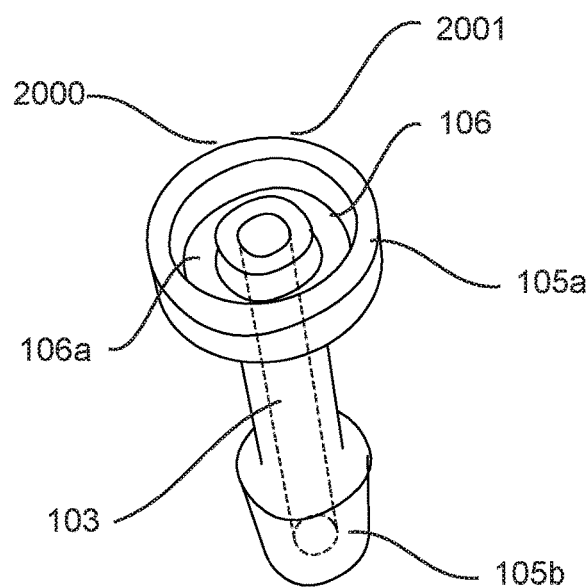
FIG. 1B illustrates a fluid pathway formed in the first vaporization element.
Figure 1C:
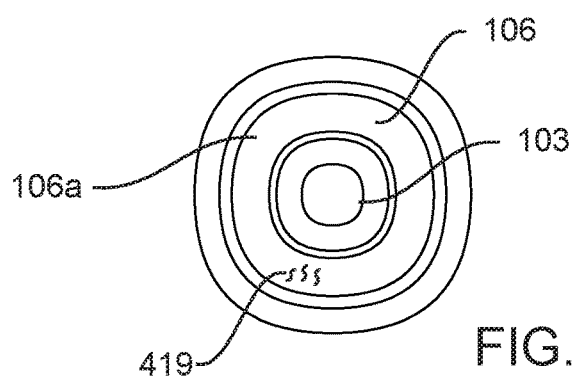
FIG. 1C illustrates a top view of the first vaporization element.

Referring to FIG. 1A, the vaporization element 2000, in the form of a first vaporization element 2001, is shown in perspective view and is formed from an elongated hollow member 105 that is made from a low thermal conductivity material, such as ceramic, and having a first end 105a and a second end 105b opposite the first end 105a, a fluid pathway 103 (as seen in FIG. 1B) propagates through the elongated hollow member 105 from the first end 105a to the second end 105b thereof. The second end 105b is for coupling with the waterpipe input port 421b, as shown in FIGS. 2A and 3A.

The vaporization element 2000 has an annular heating element 106 having a first side 106a and a second side 106b (FIG. 1D) opposite the first side 106a, the annular heating element 106 is thermally coupled with the elongated hollow member 105 proximate the first end 105a having the first side 106a facing the first end 105a with the fluid pathway 103 propagating through a center thereof (as seen in FIG. 1B), the annular heating element 106 comprises a first electrical contact 107 and a second electrical contact 108 proximate the second side 106b. The annular heating element 106 secured to the elongated hollow member 105 for allowing thermal expansion thereof along a radial axis perpendicular to the fluid pathway 103. Without properly securing the annular heating element 106 to the elongated hollow member 105 it is easy to crack the annular heating element 106 due to expansion forces of the elongated hollow member 105 and as such a unitary construction of the annular heating element 106 is preferable.

Referring to FIG. 1D, the annular heating element 106 comprising a resistive heater 155 disposed between the first and second electrical contacts, 107 and 108, and proximate the second side 106b. The annular heating element 106 comprises ceramic material where the resistive heater 155 comprises a metallic planar heater 168 disposed on the second side 106b between the first and second electrical contacts 107 108 for receiving of electrical energy from the electrical power source 156, wherein the thermal coupling between the annular heating element and the elongated hollow member 105 comprises silica material. Silica is also known in the art as ceramic glaze, so the coupling between the annular heating element 106 and the elongated hollow member 105 is by means of a ceramic glaze.

The electrical power source 156 is electrically coupled with the first and second electrical contacts 107 108 for providing of electrical power to the resistive heater 155 for heating of the resistive heater 155 for imparting thermal energy to the annular heating element 106.

As is evident from FIG. 1D, the vaporization element 2000 comprises a temperature sensor 170 thermally coupled with at least one of the elongated hollow member 105 and the annular heating element 106 proximate the second side 106b of the annular heating element 106, the temperature sensor 170 has a temperature signal output port 170a for providing a temperature signal in dependence upon the imparting of thermal energy to the annular heating element 106. Typically the temperature signal is based on a resistance of the temperature sensor 170 and the resistance varies inversely with respect to the temperature being sensed by the the temperature sensor 170.

Referring to FIG. 2A, the DVCPM 100 in accordance with the first embodiment of the invention is shown attached to a waterpipe 421 having an inhalation aperture 421a and an input port 421b. The vaporization element 2000, for example the first vaporization element 2001, but it is not limited to the first vaporization element 2001, the second vaporization element 2002 or the third vaporization element 2003 or the fourth vaporization element 2004, any of the vaporization elements 2000 are useable with the DVCPM 100.

In this embodiment the vaporization element 2000 is disposed within the first housing 101 and the first housing 101 frictionally engages the elongated hollow member 105 where the second end 105b of the elongated hollow member 105 couples with the waterpipe input port 421b. An electrical power source 156 (disposed within the first housing 101 and not visible from an outside thereof, but visible in FIG. 2C as the first and second batteries 111, 112) is provided and coupled with a first control circuit 113 electrically coupled with the electrical power source 156 (FIG. 2C) and the first and second electrical contacts 107 108 and the temperature signal output port 170a. The first control circuit 113 for processing of the temperature signal and for controllably providing of the electrical power to the resistive heater 155 for reaching the predetermined temperature of the annular heating element 106 second side 106b.

During heating of the resistive heater 155, a portion of the thermal energy is transferred to the annular heating element 106 first side 106a and another portion, other than the first portion, is transferred to the elongated hollow member 105 proximate the first end 105a, upon the annular heating element 106 second side 106b reaching a predetermined temperature the concentrated phyto material extract 419 is applied to the annular heating element 106 first side 106a (FIG. 1C) and becomes vaporized and upon inhalation from the inhalation aperture 421a this vapor 422 is mixed with ambient air 555 (FIG. 2A) and flows through the fluid pathway 103 from the first end 105a where it receives thermal energy proximate the coupling between the annular heating element 106 and the elongated hollow member 105 and loses thermal energy to the elongated hollow member 105 proximate the second end 105b as it propagates through the input port 421b of the waterpipe 421 and through to the inhalation aperture 421a.

Referring to FIGS. 1E and 1F, the vaporization element 2000, in the form of the second vaporization element 2002, is shown in perspective view and cutaway view, respectively, and is formed from an elongated hollow member 105 that is made from a low thermal conductivity material, such as glass or quartz, and having a first end 105a and a second end 105b opposite the first end 105a, a fluid pathway 103 (as seen in FIG. 1F) propagates through the elongated hollow member 105 from the first end 105a to the second end 105b thereof. The second end 105b is for coupling with the waterpipe input port 421b, as shown in FIGS. 2A and 3A.

The vaporization element 2000 has an annular heating element 106 having a first side 106a and a second side 106b opposite the first side 106a, the annular heating element 106 is thermally coupled with the elongated hollow member 105 proximate the first end 105a having the first side 106a facing the first end 105a with the fluid pathway 103 propagating through a center thereof (as seen in FIG. 1F), the annular heating element 106 comprising a first electrical contact 107 and a second electrical contact 108 proximate the second side 106b, the annular heating element 106 secured to the elongated hollow member 105 for allowing thermal expansion thereof along a radial axis perpendicular to the fluid pathway 103.

Referring to FIG. 1E, a cutaway view of the vaporization element 2000, in the form of the second vaporization element 2002, is shown. The annular heating element 106 comprising a resistive heater 155 disposed between the first and second electrical contacts, 107 and 108, and proximate the second side 106b. The resistive heater 155 comprises a resistance wire 169 disposed proximate the second side 106b between the first and second electrical contacts 107 108 for receiving of electrical energy from the electrical power source 156, wherein the thermal coupling between the annular heating element and the elongated hollow member 105 comprises glass or quartz.

The electrical power source 156 is electrically coupled with the first and second electrical contacts 107, 108 for providing of electrical power to the resistive heater 155 for heating of the resistive heater 155 for imparting thermal energy to the annular heating element 106.

Referring to FIG. 2A for example, when the second vaporization element 2002 is utilized and during heating of the resistive heater 155, a portion of the thermal energy is transferred to the annular heating element 106 first side 106a and another portion, other than the first portion, is transferred to the elongated hollow member 105 proximate the first end 105a, upon the annular heating element 106 second side 106b reaching the predetermined temperature the concentrated phyto material extract 419 is applied to the annular heating element 106 first side 106a (FIG. 1E) and becomes vaporized and upon inhalation from the inhalation aperture 421a this vapor 422 is mixed with ambient air 555 and flows through the fluid pathway 103 from the first end 105a where it receives thermal energy proximate the coupling between the annular heating element 106 and the elongated hollow member 105 and loses thermal energy to the elongated hollow member 105 proximate the second end 105b as it propagates through the input port 421b of the waterpipe 421 and through to the inhalation aperture 421a.

Referring to FIG. 1F, the vaporization element 2000 comprises a temperature sensor 170 thermally coupled with at least one of the elongated hollow member 105 and the annular heating element 106 proximate the second side 106b of the annular heating element 106, the temperature sensor 170 has a temperature signal output port 170a for providing a temperature signal in dependence upon the imparting of thermal energy to the annular heating element 106. In some cases uses a glass or quartz vaporization element 2000 is preferable because a user can see the resistance wire 169 heating up and it provides a glow as the predetermined temperature is reached.

Referring to FIGS. 1G and 1H, the vaporization element 2000 is shown in the form of the third vaporization element 2003. The vaporization element 2000 in the form of the third vaporization element 2003 is formed from an elongated hollow member 105 that is made from a low thermal conductivity material, such as ceramic, but can also be made from glass or quartz, and having a first end 105a and a second end 105b opposite the first end 105a, the fluid pathway 103 (as seen in FIG. 1G) propagates through the elongated hollow member 105 from the first end 105a to the second end 105b thereof. The second end 105b is for coupling with the waterpipe input port 421b, as shown in FIGS. 2A and 3A.

The vaporization element 2000 has a annular heating element 106 that is a partial annular heating element 106c that does not comprise a full three hundred and sixty degrees arc about the fluid pathway 103 when thermally coupled about the elongated hollow member 105 and has a portion thereof removed, wherein it comprise about a ninety degrees arc about the fluid pathway when disposed about the elongated hollow member 105.

The partial annular heating element 106c is radially disposed with respect to the elongated hollow member 105. As shown in FIG. 1G, the elongated hollow member 105 comprises a first aperture 105aa proximate the first end thereof 105a and a second aperture 105bb proximate the second end thereof 105b and the fluid pathway 103 formed between the first and second apertures, 105aa and 105bb, wherein the first and second apertures are axially disposed and comprises the resistive heater 155. Preferably the partial annular heating element 106c is disposed proximate the first end 105a of the elongated hollow member 105.

The partial annular heating element 106c has a first side 106a and a second side 106b opposite the first side 106a, partial annular heating element 106c is thermally coupled with the elongated hollow member 105 proximate the first end 105a having the first side 106a facing the first end 105a with the fluid pathway 103 propagating through a center thereof (as seen in FIG. 1G), the partial annular heating element 106c comprising a first electrical contact 107 and a second electrical contact 108 proximate the second side 106b, the partial annular heating element 106c secured to the elongated hollow member 105 for allowing thermal expansion thereof along a radial axis that is perpendicular to the fluid pathway 103.

Referring to FIG. 1H, the partial annular heating element 106c comprising a resistive heater 155 disposed between the first and second electrical contacts, 107 and 108, and proximate the second side 106b. The partial annular heating element 106c comprises ceramic material where the resistive heater 155 comprises a metallic planar heater 168 disposed on the second side 106b between the first and second electrical contacts 107 108 for receiving of electrical energy from the electrical power source 156, wherein the thermal coupling between the partial annular heating element 106c and the elongated hollow member 105 comprises silica material.

The electrical power source 156 is electrically coupled with the first and second electrical contacts 107 108 for providing of electrical power to the resistive heater 155 for heating of the resistive heater 155 for imparting thermal energy to the partial annular heating element 106c.

Referring to FIG. 2A, when the vaporization element 2000 in the form of the third vaporization element 2003 is coupled with the waterpipe 421, during heating of the resistive heater 155, a portion of the thermal energy is transferred to the partial annular heating element 106c first side 106a and another portion, other than the first portion, is transferred to the elongated hollow member 105 proximate the first end 105a, upon the partial annular heating element 106c second side 106b reaching the predetermined temperature the concentrated phyto material extract 419 is applied to the partial annular heating element 106c first side 106b (FIG. 1G) and becomes vaporized and upon inhalation from the inhalation aperture 421a this vapor 422 is mixed with ambient air 555 and flows through the fluid pathway 103 from the first end 105a where it receives thermal energy proximate the coupling between the partial annular heating element 106c and the elongated hollow member 105 and loses thermal energy to the elongated hollow member 105 proximate the second end 105b as it propagates through the input port 421b of the waterpipe 421 and through to the inhalation aperture 421a.

Referring to FIG. 1H, the vaporization element 2000 comprises a temperature sensor 170 thermally coupled with at least one of the elongated hollow member 105 and the partial annular heating element 106c proximate the second side 106b of the partial annular heating element 106c, the temperature sensor 170 has a temperature signal output port 170a for providing a temperature signal in dependence upon the imparting of thermal energy to the partial annular heating element 106c.

FIG. 1I illustrates a variation of the third vaporization element 2003 having the partial annular heating element 2003 in the form of a fourth vaporization element 2004, whereby the resistive heater 155 (not visible in this FIG. 1I) is disposed between the first and second electrical contacts, 107 and 108, is at a distance, for example 20 mm, from an axial center of the first end 105a of the elongated hollow member 105. Whereby in comparison, for the third vaporization element 2003 the resistive heater 155 is approximately 6 mm away from the axial center of the first end 105a of the elongated hollow member 105.

Furthermore, the fluid pathway 103 is curved between the first end 105a and the second end 105b. Such a variation may be preferable so that thermal transfer from the fourth vaporization element 2004 to the elongated hollow member 105 (e.g. a hollow ceramic member) is reduced as well the fourth vaporization element 2004 provides for a lower thermal inertia than the first vaporization element 2001.

The elongated hollow member 105 comprises a first aperture 105aa proximate the first end thereof 105a and a second aperture 105bb proximate the second end thereof 105b and the fluid pathway 103 formed between the first and second apertures, wherein the first and second apertures 105aa and 105bb are other than axially disposed and preferably central axes of the first and second apertures 105aa and 105bb are perpendicular to each other.

In this fourth vaporization element 2004 the resistive heater 155 is radially disposed away from the elongated hollow member 105, which therefore results in a bend in the fluid pathway 103. Using the fourth vaporization element 2004 is sometimes preferable as it allows for an elongated path length for the fluid pathway 103 and as such improved cooling for the vapor 422 as it propagates through the fluid pathway 103. If the fourth vaporization element 2004 uses quartz material then the resistive heater 155 is envisaged comprising a pancake ceramic heater or a resistance wire 169. If the fourth vaporization element 2004 uses a ceramic material then the resistive heater 155 is envisaged comprising a metallic planar heater 168 that is sintered onto the ceramic.

Figure 2B:
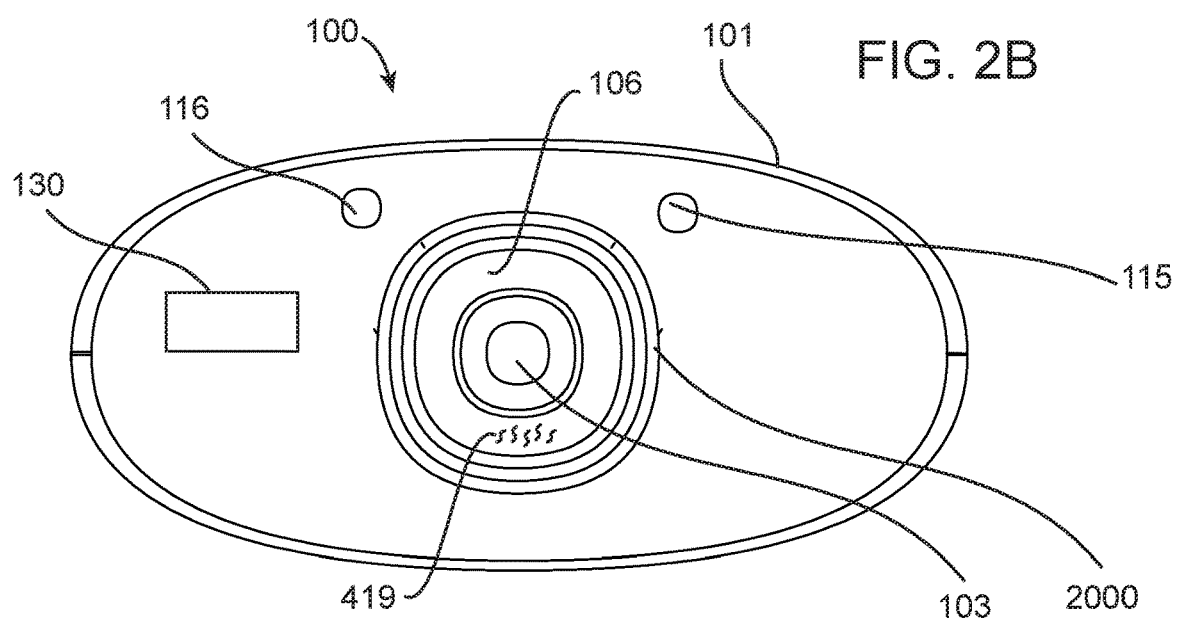
FIG. 2B illustrates a device for vaporization of concentrated phyto material extracts in accordance with the first embodiment of the invention from a top view.
Figure 2C:
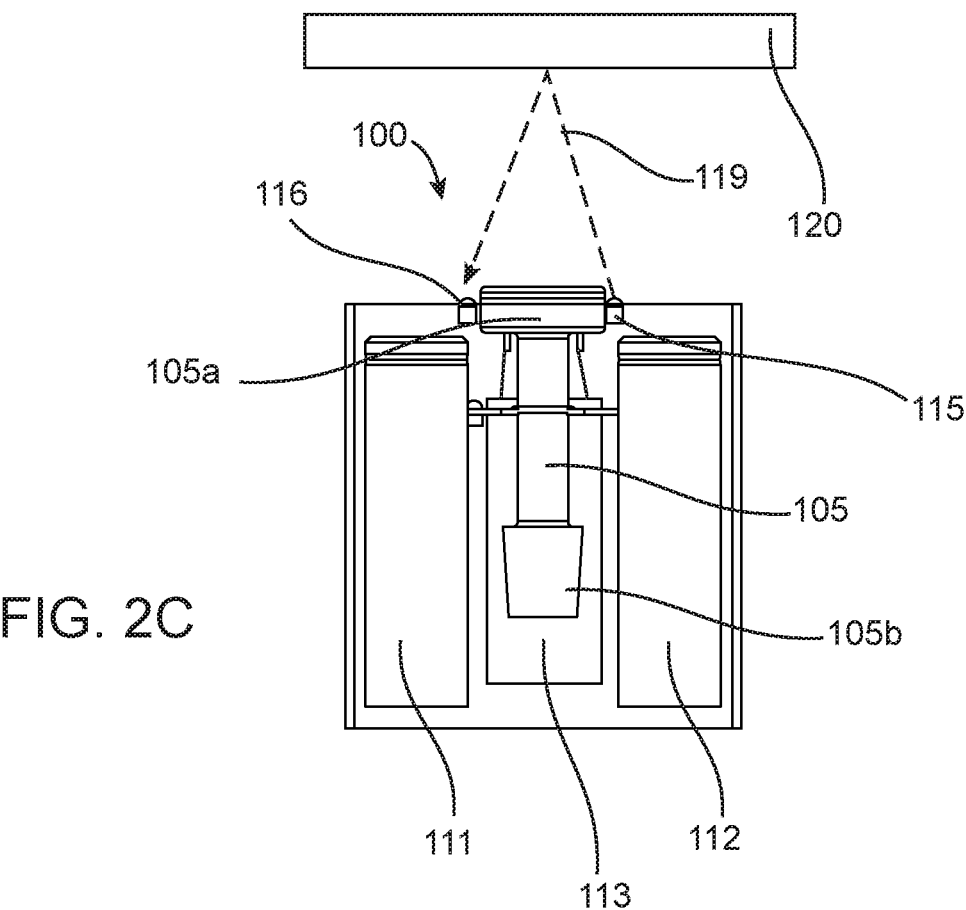
FIG. 2C illustrates a device for vaporization of concentrated phyto material extracts in accordance with the first embodiment of the invention from an opened front view.
Figure 2D:
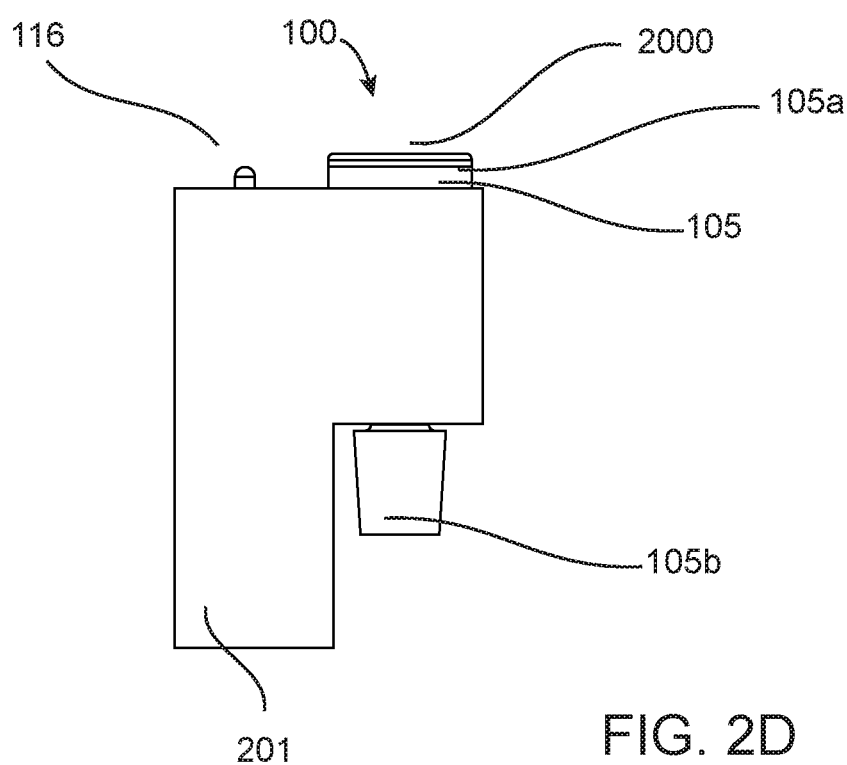
FIG. 2D illustrates a device for vaporization of concentrated phyto material extracts in accordance with the first embodiment of the invention from a side view.

Referring to FIG. 2A and in conjunction with FIGS. 2A, 2B and 2D a first infrared transmitter 115 is envisaged for protruding past the first housing 101 proximate the first end 105a of the vaporization element 2000. FIG. 2B illustrates a top view and FIG. 2C illustrates an internal front view and FIG. 2D illustrates a closed side view.

A first infrared receiver 116 is provided for protruding past the first housing 101 proximate the first end 105a of the vaporization element 2000, the first infrared transmitter 115 and the first infrared receiver 116 are electrically coupled with the first control circuit 113, the first infrared transmitter 115 for sending out a first infrared signal 119 for being reflected from an infrared signal reflective member 120 for being received by the first infrared receiver 116 for enabling the heating of the annular heating element 106 (e.g. an annular ceramic heating element) and for other than being received by the first infrared receiver 116 when the infrared signal reflective member 120 is other than present, upon heating of the annular heating element 106, the concentrated phyto material extract 419 is heated to the predetermined temperature and becomes vaporized and this vapor 422 and is mixed with ambient air 555 and flows through the fluid pathway 103, as illustrated in FIG. 2A.

Preferably the infrared signal reflective member 120 is in the form of a hand, whereby when the hand of a user is waived over the top of the DVCPM 100, this activates the first control circuit 113 for heating of the vaporization element 2000. Referring to FIG. 2C, a first battery 111 and a second battery 112 are shown as part of the electrical power source 156. Any of the vaporization elements 2000 in the form of the first through fourth, 2001 through 2004, are envisaged to work with the first infrared transmitter 115 and the first infrared receiver 116.

Figure 3B:
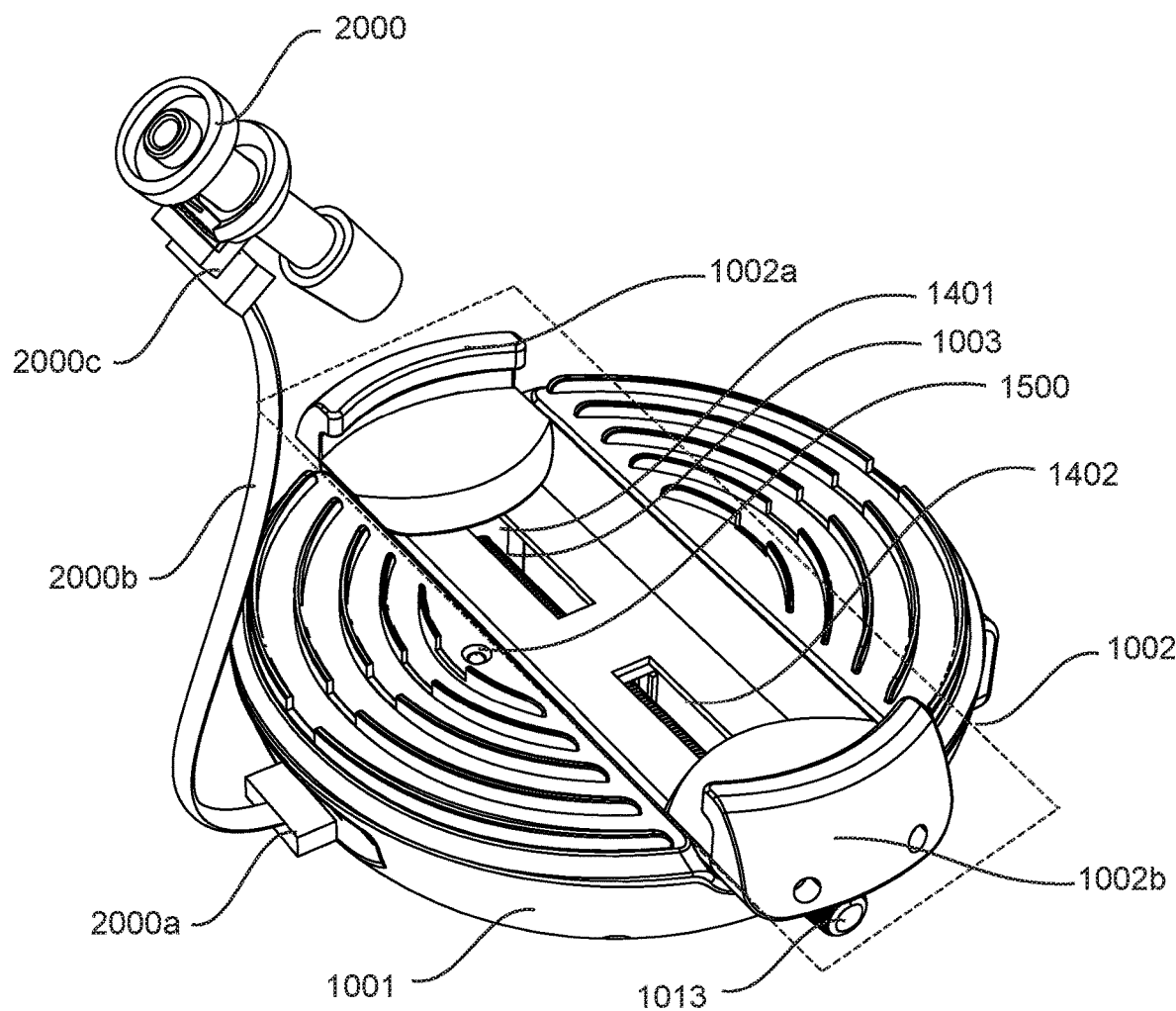
FIG. 3B illustrates a device for vaporization of concentrated phyto material extracts in accordance with the second embodiment of the invention and showing an adjustable clamping mechanism.

FIG. 3A illustrates a device for vaporization of concentrated phyto material extracts 1000 (DVCPM) in accordance with a second embodiment of the invention. The DVCPM 1000 is for attaching to a waterpipe 421 having an input port 421b and an inhalation aperture 421a with a waterpipe fluid pathway 8989 formed therebetween. The DVCPM 1000 includes the vaporization element 2000 having the second end 105b coupled with the input port 421b. The waterpipe 421 has a first housing 1001 for preferably having the an electrical power source 156 contained therein, the first housing 1001 comprising an adjustable clamping mechanism 1002, as is shown in FIG. 3B, for frictionally engaging of the waterpipe 421.

FIG. 3A furthermore illustrates a vaporization element first coupling port 2000a electrically coupled with the first control circuit 113 (FIG. 3C) and vaporization element second coupling port 2000c electrically coupled with the vaporization element 2000 first and second electrical contacts 107 108 and the temperature signal output port 170a.

Figure 3J:
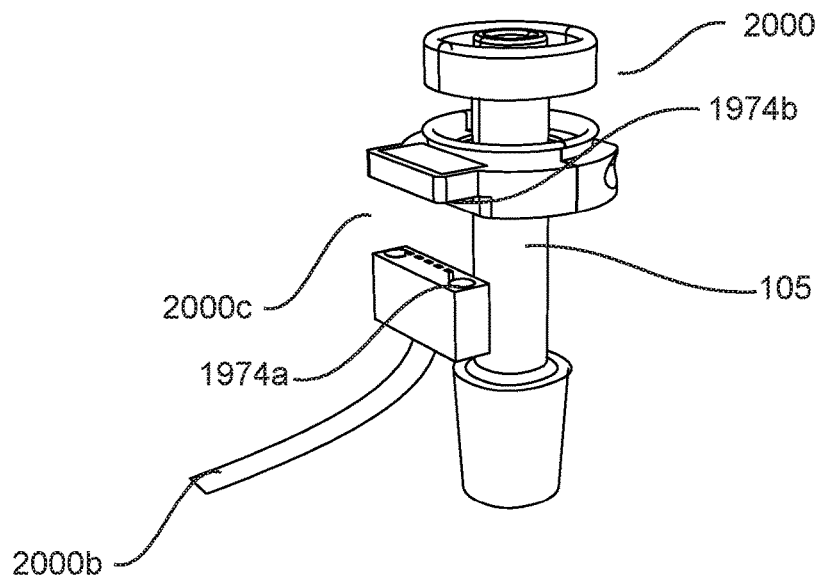
FIG. 3C illustrates a device for vaporization of concentrated phyto material extracts in accordance with the second embodiment of the invention and showing a lead screw for adjusting of the adjustable clamping mechanism.
FIG. 3D illustrates a device for vaporization of concentrated phyto material extracts in accordance with the second embodiment of the invention and showing a control panel in a first position.
FIG. 3E illustrates a device for vaporization of concentrated phyto material extracts in accordance with the second embodiment of the invention and showing a control panel in a second position.
FIG. 3F illustrates a device for vaporization of concentrated phyto material extracts in accordance with the second embodiment of the invention and showing the adjustable clamping mechanism being frictionally engaged to a first diameter base waterpipe.
FIG. 3G illustrates a device for vaporization of concentrated phyto material extracts in accordance with the second embodiment of the invention and showing the adjustable clamping mechanism being frictionally engaged to a second diameter base waterpipe.
FIG. 3H illustrates a device for vaporization of concentrated phyto material extracts in accordance with the second embodiment of the invention and showing a plurality of batteries contained therein.
FIG. 3I illustrates a device for vaporization of concentrated phyto material extracts in accordance with the second embodiment of the invention and showing various input and output ports; and, FIG. 3J a device for vaporization of concentrated phyto material extracts in accordance with the second embodiment of the invention having a first magnet and a second magnet as part of the a second coupling port.
Figure 3I:
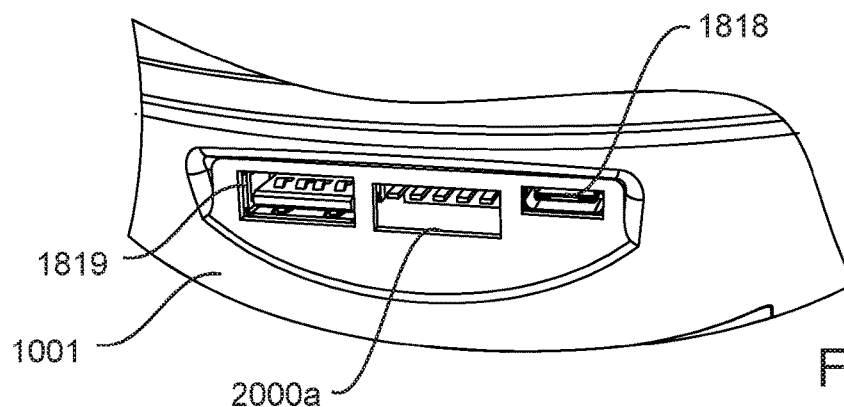
Figure 3C:
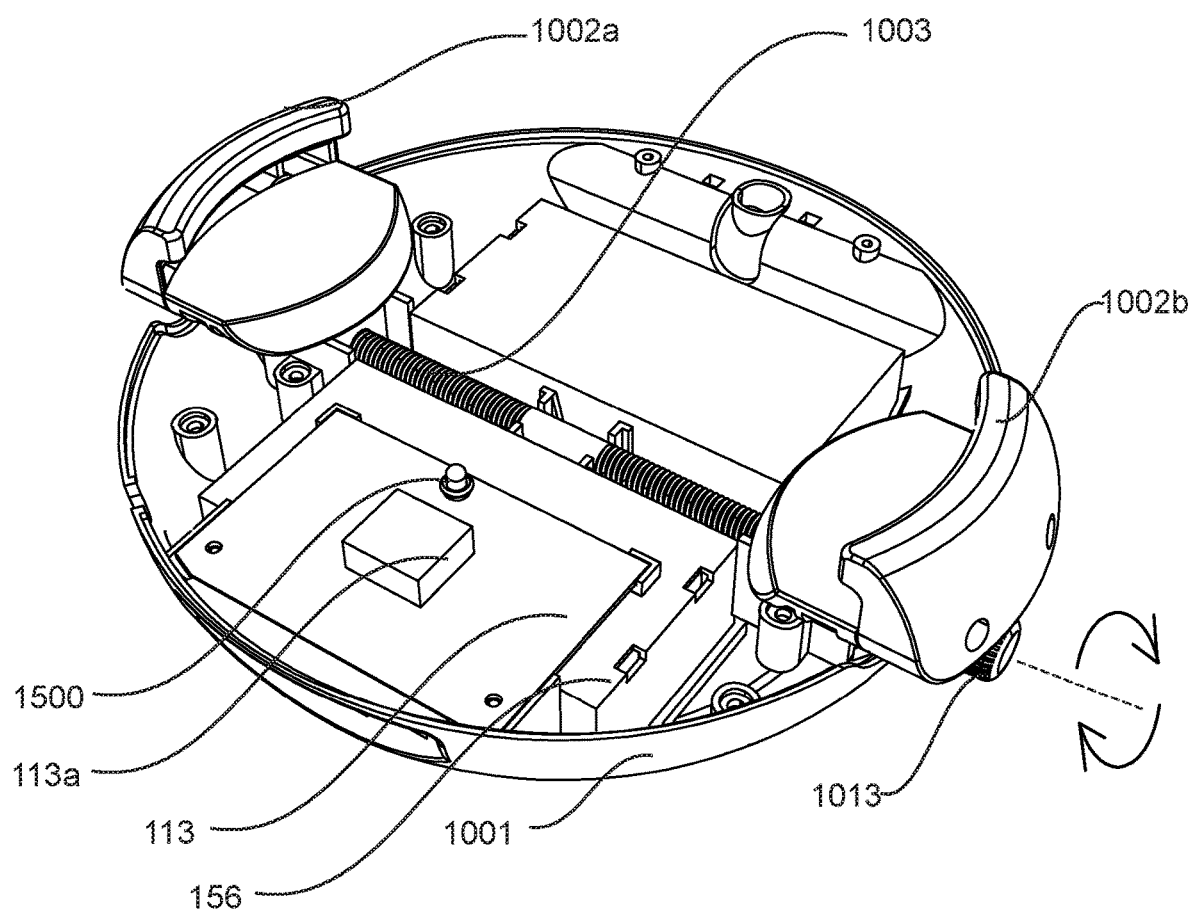

A vaporization element connector cable 2000b is electrically coupled between the vaporization element first coupling port 2000a and the vaporization element second coupling port 2000c, the vaporization element connector cable 2000b is for electrically coupling of the vaporization element 2000 with the first control circuit 113 (FIG. 3C).

Preferably the vaporization element connector cable 2000b is magnetically and electrically coupled with the vaporization element whereby the second coupling port 2000c comprises a magnetic coupling. FIG. 3j illustrates a first magnet 1974a and a second magnet 1974b whereby the second coupling port 2000c is electrically and mechanically held together using the first and second magnets 1974a and 1974b. However a standard pin connector is also envisaged as would be obvious to one skilled in the art.

Referring to FIG. 3B, the adjustable clamping mechanism 1002 comprises a first jaw 1002a and a second jaw 1002b disposed opposite the first jaw 1002a, the first and second jaws are mechanically coupled to a lead screw 1003, for upon rotating of the lead screw 1003 in a clockwise direction for increasing a frictional engagement of the waterpipe 421 and for upon rotating of the lead screw in a counter clockwise direction for decreasing a frictional engagement of the waterpipe 421, wherein a spacing between the first jaw 1002a and the second jaw 1002b varies between 6 cm and 15 cm, the first and second jaws 1002a and 1002b for respectively sliding within a first track 1401 and a second track 1402. A thumb screw 1013 is provided and frictionally coupled with the lead screw 1003 and at least partially protruding past the first housing 1001 for being turned to adjust the lead screw 1003.

This allows the end user the possibility to adjust the adjustable clamping mechanism 1002 to accommodate various water pipe bases. FIG. 3F illustrates the waterpipe 421 as a first diameter base waterpipe 421a being frictionally engaged by the adjustable clamping mechanism 1002 when the first and second jaws 1002a and 002b are in a first position and FIG. 3G illustrates the waterpipe 421 as a second diameter base waterpipe 421b being frictionally engaged by the adjustable clamping mechanism 1002 when the first and second jaws 1002a and 1002b are in a second position. Because the second diameter base waterpipe 421b is of a larger diameter than the first diameter base waterpipe 421a, a spacing between the first and second jaws is larger in the second position than the first position. Additionally shown in FIG. 3F is a plurality of deformable ribs 8888 used for assisting in frictionally contacting the waterpipe 421 when its frictionally engaged by the adjustable clamping mechanism 1002.

A three colored LED 1500 is also provided and protrudes past the first housing 1001 and is optically aimed at the waterpipe 421. The LED 1500 electrically coupled with the first control circuit 113, the LED 1500 for directing light towards the waterpipe 421 and for changing color in dependence upon the temperature signal. For example the LED 1500 has a blue color when a temperature of the resistive heater 155 is around 200 degrees Fahrenheit and has a red color when the temperature of the resistive heater 155 is around 600 degrees Fahrenheit.

Referring to FIG. 3C, the first control circuit 113 electrically coupled with the electrical power source 156 and the first and second electrical contacts 107 108 of the vaporization element and the temperature signal output port 170a, the first control circuit 131 includes a first processor 113a for processing of the temperature signal and for controllably providing of the electrical power to the resistive heater 155 for reaching the predetermined temperature.

Figure 3D:
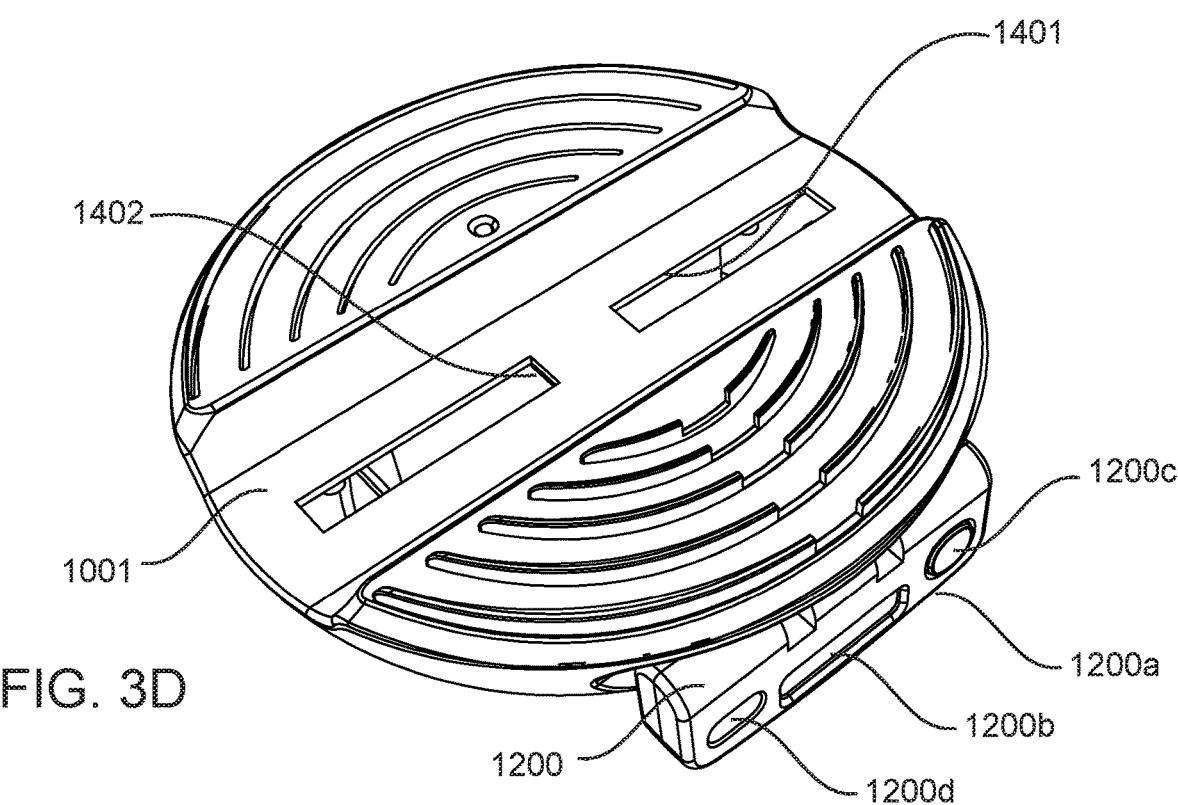
Figure 3E:
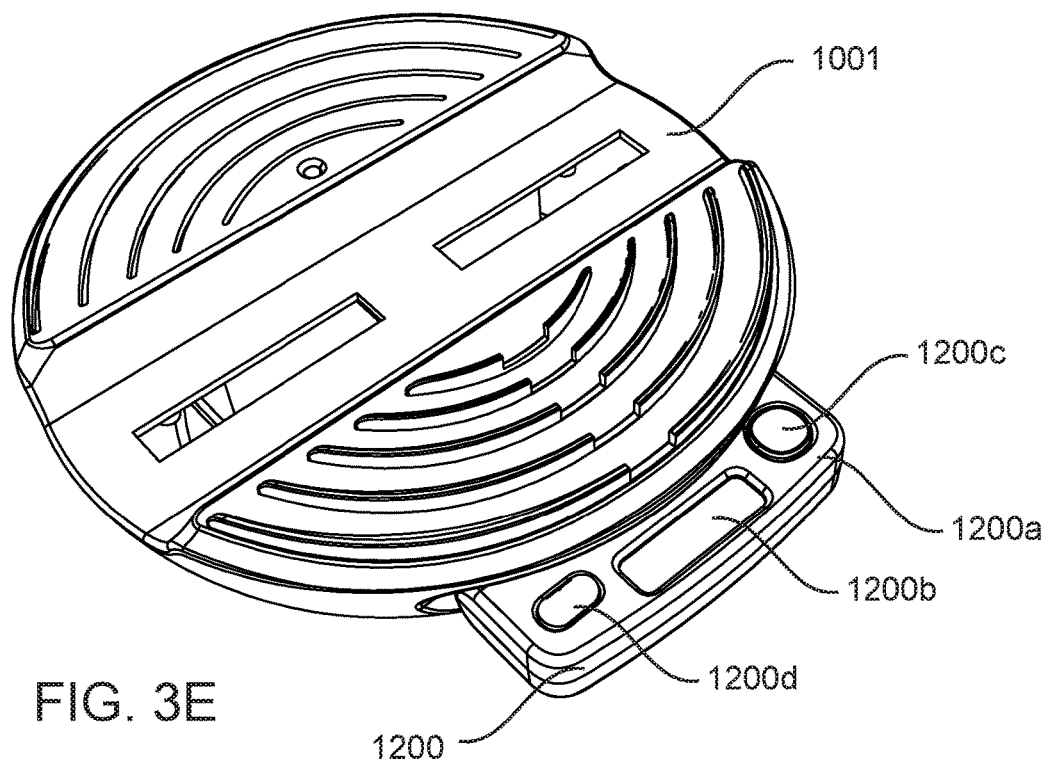
Figure 3F:
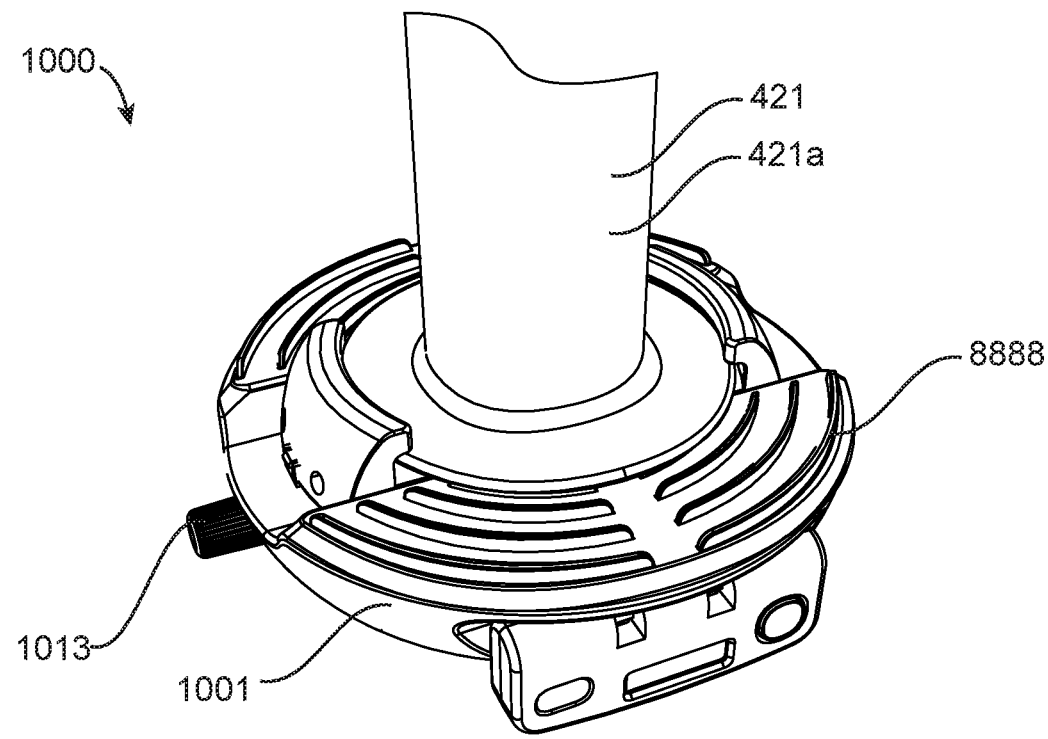
Figure 3G:
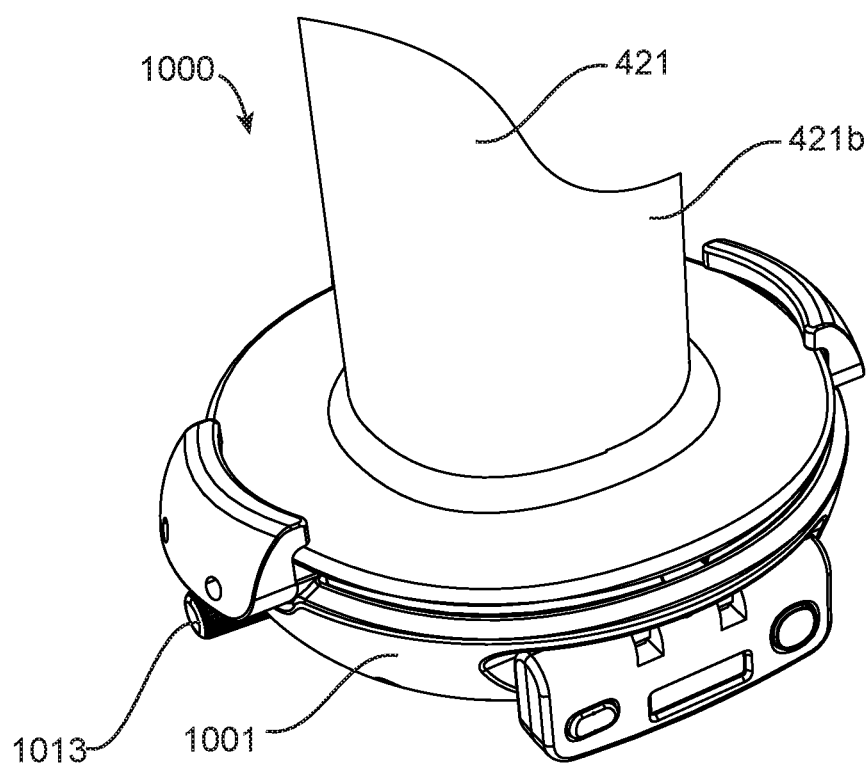

Referring to FIGS. 3D and 3E, a control panel 1200 is provided having a control surface 1200a, the control panel 1200 is rotationally coupled with the first housing 1001, the control panel being hinged with the first housing 1001 for operating between a first position (FIG. 3D) and a second position (FIG. 3E), wherein in the first position the control surface 1200a is approximately perpendicular to the first track 1401 and the second track 1402 and where in the second position the control surface 1200a is approximately parallel to the first track 1401 and the second track 1402.

Furthermore, the control panel 1200 comprises an OLED display screen 1200b electrically coupled with the first control circuit 113 for displaying a temperature in dependence upon the temperature control signal and an activation button 1200c electrically coupled with the first control circuit 113 for enabling operation of the first control circuit 113 and a temperature adjustment rocker button 1200d electrically coupled with the first control circuit 113 for adjusting the predetermined temperature from, for example 100 degrees Celsius to 400 degrees Celsius.

Figure 3H:
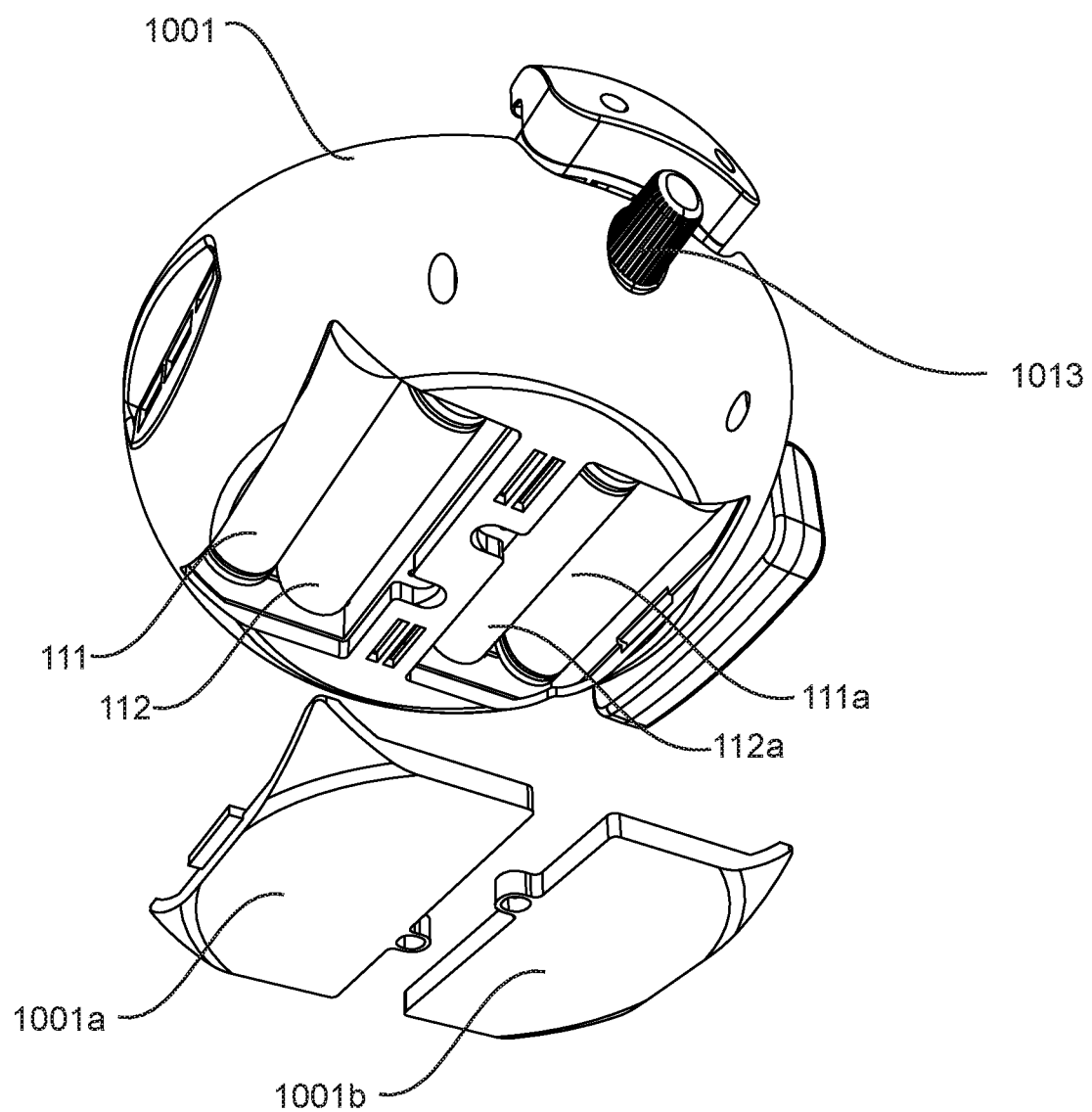

FIG. 3H illustrates the DVCPM 1000 from a bottom view of the first housing 1001 and showing a plurality of batteries 111, 112, 111a, 112a as the electrical power source 156, the plurality of batteries 111, 112, 111a, 112a electrically coupled in series and electrically coupled with the first control circuit 113, wherein the first housing 1001 comprises a first battery door 1001a and a second battery door 1001b, wherein the batteries 111 and 112 are removable through the first battery door 1001a and the batteries 111a and 112a are removable through the second battery door 1001b.

FIG. 3I illustrates the DVCPM 1000 with various input and output ports, such as a USB-C port 1818 for receiving of electrical energy from a recharger (not shown) and a USB port 1819 for providing of electricity from the electrical power source 156 to connected external devices for being recharged, such as a cellular phone. The vaporization element first coupling port 2000a is also oriented proximate the USB-C and the USB port and these ports are electrically coupled with the first control circuit 113. The DVCPM 1000 thus can also act as a portable battery bank for recharging other electrical devices and for storing electrical energy therein for portable heating of the vaporization element 2000.

Having a device for vaporization of concentrated phyto material extracts in accordance with the first and second embodiments of the invention 100 and 1000, respectively, allows for a reduction in potential harm from combustion of the phyto material extracts 419. Furthermore it allows for a portable device that overcomes the deficiencies in the prior art. Having the vaporization element 2000 manufactured from ceramic or glass or quartz allows for easy cleaning. Also because this vaporization element 2000 is manufactured from a low thermal conductivity material allows for the second end 105b thereof to be substantially cooler than the first end 105a, thus allowing the elongated hollow member 105 to provide additional cooling to the vapors 421 and ambient air 555 when propagating therethrough.

Ceramic and glass materials are also easy to clean and do not typically stain when used for vaporization of phyto material extracts 419. The LED 1500 advantageously provides for an indication to the end user of the approximate temperature of the vaporization element 2000. Preferably the electrical power source 156 is from internal battery power, however a wall adapter is also envisaged.

Numerous other embodiments are envisaged without departing from the spirit or scope of the invention.

What I claim is:

1. A device for vaporization of concentrated phyto material extracts, the device attachable to a waterpipe having an input port and an inhalation aperture with a waterpipe fluid pathway formed therebetween, the device comprising:
    a vaporization element comprising:
    an elongated hollow member formed from a low thermal conductivity material having a first end and a second end opposite the first end, a fluid pathway propagating through the elongated hollow member from the first end to the second end thereof, wherein the second end is engageable with the waterpipe input port;
    an annular heating element having a first side and a second side opposite the first side, the annular heating element thermally coupled with the elongated hollow member proximate the first end and having the first side facing the first end with the fluid pathway propagating through a center thereof, the annular heating element comprising a first electrical contact and a second electrical contact proximate the second side, the annular heating element secured to the elongated hollow member and allowing thermal expansion thereof along a radial axis perpendicular to the fluid pathway, the annular heating element comprising a resistive heater disposed between the first and second electrical contacts and proximate the second side; and
    an electrical power source electrically coupled with the first and second electrical contacts for providing electrical power to the resistive heater to heat the resistive heater and thereby impart thermal energy to the annular heating element,
    wherein during heating of the resistive heater, a first portion of the thermal energy is transferred to the annular heating element first side and a second portion, other than the first portion, is transferred to the elongated hollow member proximate the first end, and upon the annular heating element second side reaching a predetermined temperature and the concentrated phyto material extract being applied to the annular heating element first side, the concentrated phyto material extract is vaporized and upon inhalation from the inhalation aperture this vapor is mixed with ambient air and flows through the fluid pathway from the first end where it loses thermal energy to the elongated hollow member proximate the second end as it propagates through the input port of the waterpipe and through the waterpipe fluid pathway through to the inhalation aperture.

2. A device for vaporization of concentrated phyto material extracts according to claim 1 wherein the elongated hollow member formed from a low thermal conductivity material comprises ceramic material and the annular heating element comprises ceramic material where the resistive heater comprises a metallic planar heater disposed on the second side between the first and second electrical contacts and configured to receive electrical energy from the electrical power source, wherein the thermal coupling between the annular heating element and the elongated hollow member comprises silica.

3. A device for vaporization of concentrated phyto material extracts according to claim 1 wherein the elongated hollow member formed from a low thermal conductivity material comprises glass material and the annular heating element comprises glass material where the resistive heater comprises a resistance wire disposed on the second side between the first and second electrical contacts for receiving of electrical energy from the electrical power source, wherein the thermal coupling between the annular heating element and the elongated hollow member comprises glass.

4. A device for vaporization of concentrated phyto material extracts according to claim 1 comprising a temperature sensor thermally coupled with at least one of the elongated hollow member and the annular heating element proximate the second side of the annular heating element, the temperature sensor having a temperature signal output port operable to provide a temperature signal in dependence upon the imparting of thermal energy to the annular heating element.

5. A device for vaporization of concentrated phyto material extracts according to claim 4 comprising:
    a first control circuit electrically coupled with the electrical power source and the first and second electrical contacts and the temperature signal output port, the first control circuit comprising a first processor operable to process the temperature signal and to controllably provide the electrical power to the resistive heater in order to reach the predetermined temperature of the annular heating element second side.

6. A device for vaporization of concentrated phyto material extracts according to claim 5 comprising:
    a vaporization element first coupling port electrically coupled with the first control circuit;
    a vaporization element second coupling port electrically coupled with the vaporization element first and second electrical contacts and the temperature signal output port; and
    a vaporization element connector cable electrically coupled between the vaporization element first coupling port and the vaporization element second coupling port, the vaporization element connector cable operable to electrically couple the vaporization element with the first control circuit.

7. A device for vaporization of concentrated phyto material extracts according to claim 5 comprising:
    a multi-colored LED electrically coupled with the first control circuit, the multi-colored LED positioned to direct light towards the waterpipe and operable to color in dependence upon the temperature signal.

8. A device for vaporization of concentrated phyto material extracts according to claim 1 wherein the annular heating element comprises a partial annular heating element that omits a portion of a full three hundred and sixty degrees arc about the fluid pathway when thermally coupled about the elongated hollow member, wherein the partial annular heating element comprises a ninety degrees arc about the fluid pathway when disposed about the elongated hollow member, the partial annular heating element comprising the resistive heater.

9. A device for vaporization of concentrated phyto material extracts according to claim 8 wherein the elongated hollow member comprises:
    a first aperture proximate the first end thereof;
    a second aperture proximate the second end thereof; and
    wherein the fluid pathway is formed between the first and second apertures, wherein the first and second apertures are axially disposed.

10. A device for vaporization of concentrated phyto material extracts according to claim 8 wherein the elongated hollow member comprises:
   a first aperture proximate the first end thereof; and
   a second aperture proximate the second end thereof; and
   wherein the fluid pathway is formed between the first and second apertures, wherein the first and second apertures are other than axially disposed and the resistive heater is radially disposed from the elongated hollow member second aperture and proximate the first aperture.

11. A device for vaporization of concentrated phyto material extracts according to claim 1 comprising a first housing enclosing the electrical power source, the first housing comprising an adjustable clamping mechanism operable to frictionally engage the waterpipe.

12. A device for vaporization of concentrated phyto material extracts according to claim 11 wherein the adjustable clamping mechanism comprises a first jaw and a second jaw disposed opposite the first jaw, the first and second jaws mechanically coupled to a lead screw, wherein rotation of the lead screw in a clockwise direction increases a frictional engagement of the waterpipe and rotation of the lead screw in a counter clockwise direction decreases the frictional engagement of the waterpipe, wherein a spacing between the first jaw and the second jaw is variable between 6 cm and 15 cm, and the first and second jaws are each operable to slide within a first track and a second track respectively.

13. A device for vaporization of concentrated phyto material extracts according to claim 12 comprising a thumb screw frictionally coupled with the lead screw, the thumb screw at least partially protruding past the first housing, the thumb screw being turnable to engage the lead screw.

14. A device for vaporization of concentrated phyto material extracts according to claim 12 comprising a control panel having a control surface, the control panel rotationally coupled with the first housing, the control panel being hinged with the first housing for operating between a first position and a second position, wherein in the first position the control surface is approximately perpendicular to the first track and the second track and where in the second position the control surface is approximately parallel to the first track and the second track.

15. A device for vaporization of concentrated phyto material extracts according to claim 14 wherein the control panel comprises:
   an OLED display screen electrically coupled with the first control circuit for displaying a temperature in dependence upon the temperature control signal;
   an activation button electrically coupled with the first control circuit for enabling operation of the first control circuit; and
   a temperature adjustment rocker button electrically coupled with the first control circuit for adjusting the predetermined temperature from 200 degrees Celsius to 400 degrees Celsius.

16. A device for vaporization of concentrated phyto material extracts according to claim 1 wherein the electrical power source comprises:
   a plurality of batteries electrically coupled in series and electrically coupled with the first control circuit, wherein the first housing comprises a first battery door and a second battery door, wherein the batteries are removable through the first battery door and the batteries are removable through the second battery door.

17. A device for vaporization of concentrated phyto material extracts according to claim 1 comprising:
   a first infrared transmitter protruding past the first housing portion proximate the first end of the elongated hollow member; and
   a first infrared receiver protruding past the first housing portion proximate the first end of the elongated hollow ceramic member, the first infrared transmitter and the first infrared receiver electrically coupled with the first control circuit, the first infrared transmitter operable to send out a first infrared signal to be reflected from an infrared signal reflective member and received by the first infrared receiver to enable heating of the vaporization element and wherein the first infrared signal is not received by the first infrared receiver when the infrared signal reflective member is not present, upon heating of the vaporization element.

18. A device for vaporization of concentrated phyto material extracts, the device attachable to a waterpipe having an input port and an inhalation aperture with a waterpipe fluid pathway formed therebetween, the device comprising:
   a vaporization element comprising:
   an elongated hollow member formed from a low thermal conductivity material having a first end and a second end opposite the first end, a fluid pathway propagating through the elongated hollow member from the first end to the second end thereof, wherein the second end is engageable with the waterpipe input port;
   an annular heating element having a first side and a second side opposite the first side, the annular heating element thermally coupled with the elongated hollow member proximate the first end and having the first side facing the first end with the fluid pathway propagating through a center thereof, the annular heating element comprising a first electrical contact and a second electrical contact proximate the second side, the annular heating element secured to the elongated hollow member using silica and allowing thermal expansion of the annular heating element along a radial axis perpendicular to the fluid pathway, the annular heating element comprising a metallic planar heater disposed on the second side between the first and second electrical contacts;
   an electrical power source comprising a plurality of batteries electrically coupled with a first control circuit, which is electrically coupled with the first and second electrical contacts for controllably providing electrical power to the metallic planar heater to heat the metallic planar heater and thereby impart thermal energy to the annular heating element,
   wherein during heating of the metallic planar heater, a first portion of the thermal energy is transferred to the annular heating element first side and a second portion, other than the first portion, is transferred to the elongated hollow member proximate the first end, and upon the annular heating element second side reaching a predetermined temperature and the concentrated phyto material extract being applied to the annular heating element first side, the concentrated phyto material extract is vaporized and upon inhalation from the inhalation aperture this vapor is mixed with ambient air and flows through the fluid pathway from the first end where loses thermal energy to the elongated hollow member proximate the second end as it propagates through the input port of the waterpipe and through the waterpipe fluid pathway and through to the inhalation aperture; and a first housing containing the electrical power source and the plurality of batteries, the first housing comprising an adjustable clamping mechanism operable to frictionally engage the waterpipe.

19. A device for vaporization of concentrated phyto material extracts according to claim 18 wherein the elongated hollow member formed from a low thermal conductivity material comprises ceramic material and the annular heating element comprises ceramic material where the resistive heater comprises a metallic planar heater disposed on the second side between the first and second electrical contacts for receiving of electrical energy from the electrical power source, wherein the thermal coupling between the annular heating element and the elongated hollow member comprises silica.

20. A device for vaporization of concentrated phyto material extracts according to claim 19 comprising:
    a temperature sensor electrically coupled with the first control circuit and thermally coupled with at least one of the elongated hollow member and the annular heating element proximate the second side of the annular heating element, the temperature sensor having a temperature signal output port for providing a temperature signal in dependence upon the imparting of thermal energy to the annular heating element.

21. A device for vaporization of concentrated phyto material extracts according to claim 18 wherein the elongated hollow member formed from a low thermal conductivity material comprises glass material and the annular heating element comprises glass material where the resistive heater comprises a resistance wire disposed on the second side between the first and second electrical contacts for receiving of electrical energy from the electrical power source, wherein the thermal coupling between the annular heating element and the elongated hollow member comprises glass.

22. A device for vaporization of concentrated phyto material extracts comprising:
    a housing comprising an electrical power source and a control circuit;
    an inhalation unit that is detachably attachable to the housing, the inhalation unit comprising a fluid chamber, an inhalation aperture, a vapor input port and a unit fluid pathway extending between the vapor input port and the inhalation aperture, wherein the fluid chamber defines a water volume within which water is receivable and the unit fluid pathway extends through the fluid chamber; and
    a vaporization unit that is detachably attachable to the housing, wherein the vaporization unit comprises a heating unit having a first surface defining a phyto material receiving area and a second surface opposite to the first surface, the heating unit comprising a heater positioned to contact the second surface, the vaporization unit includes at least two electrical contacts connected to the heater and extending axially away from the second surface, wherein the phyto material receiving area has a vapor outlet that is axially spaced apart from the first surface and the first surface comprises a ceramic material;
    wherein
    when the vaporization unit is attached to the housing and the inhalation unit is attached to the housing,
        the vapor outlet is in fluid communication with the vapor input port and a continuous flow path is defined between the phyto material receiving area and the inhalation aperture;
        the heater is connected to the electrical power source through the at least two electrical contacts;
        the control circuit is operable to controllably provide electrical power from the electrical power source to the heater and thereby heat the heater whereby thermal energy is transferred to the first surface to heat the first surface to a predefined vaporization temperature.

\* \* \* \* \*